United States Patent [19]
Ruthven, Jr.

[11] Patent Number: 4,733,658
[45] Date of Patent: Mar. 29, 1988

[54] SURGICAL SLING

[76] Inventor: James Ruthven, Jr., 42 Howard St., Rockland, Mass. 02370

[21] Appl. No.: 71,637

[22] Filed: Jul. 9, 1987

[51] Int. Cl.⁴ .................................... A61F 5/40
[52] U.S. Cl. ........................ 128/94; 128/134; 604/304
[58] Field of Search ............... 128/77, 78, 80 A, 94, 128/96, 98, 99, 102, 111, 130, 136, 138 R, 154, 155, 169, 170, 171, 133, 134, 135

[56] References Cited
U.S. PATENT DOCUMENTS
2,549,703  4/1951  New .................................. 128/94

Primary Examiner—Robert A. Hafer
Assistant Examiner—Charles H. Sam

[57] ABSTRACT

A one-piece pad of a generally L-shape provides a reversible sling. The pad is formed with a head-receiving opening and includes on each of its sides a plurality of attachment means. A two-part folding action forms a sling for either arm, wrist, or hand. The sling immobilizes the injured arm, wrist, or hand in an upwardly inclined position wherein the hand is above the heart and also provides a comfortable elbow support.

10 Claims, 6 Drawing Figures

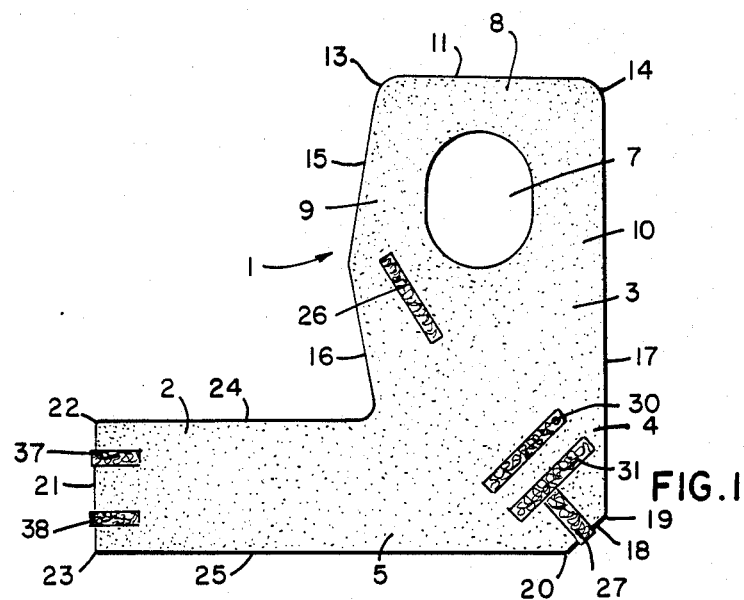
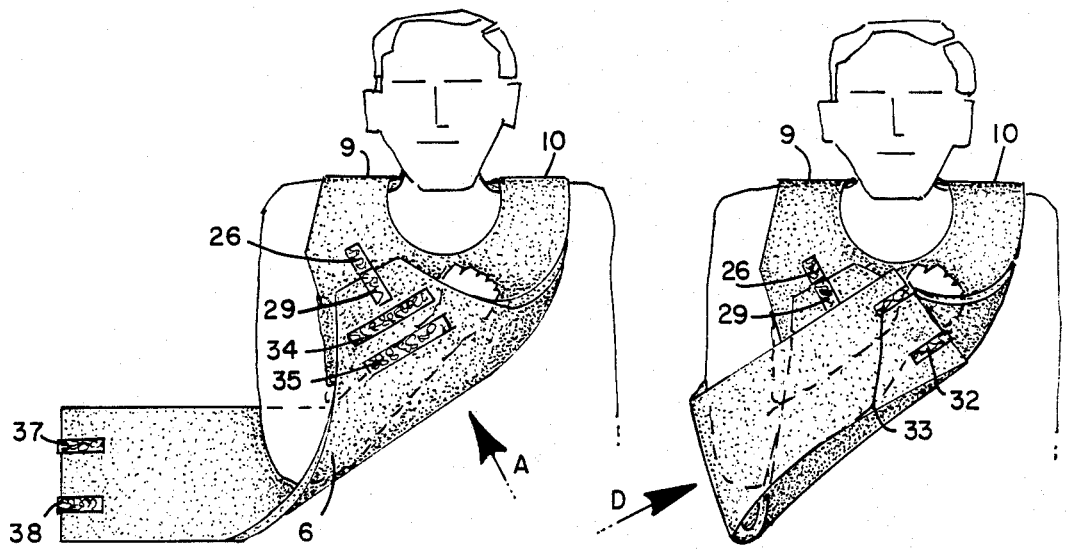
FIG. 1
FIG. 2
FIG. 3

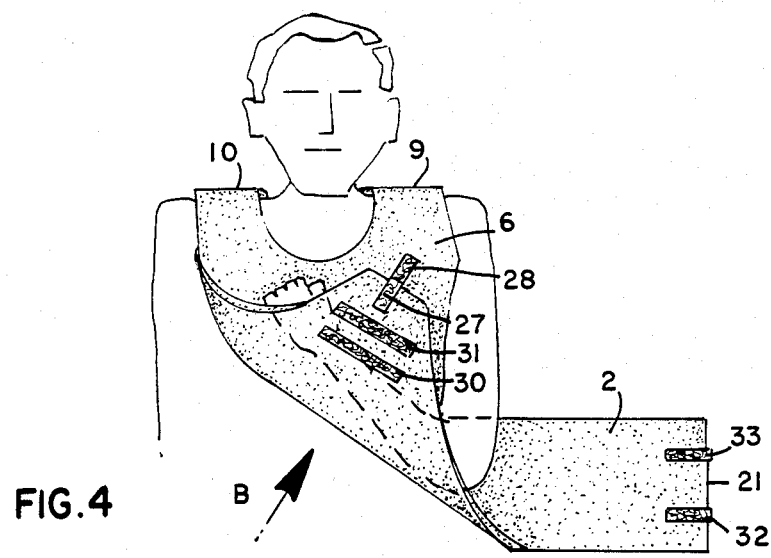
FIG. 4
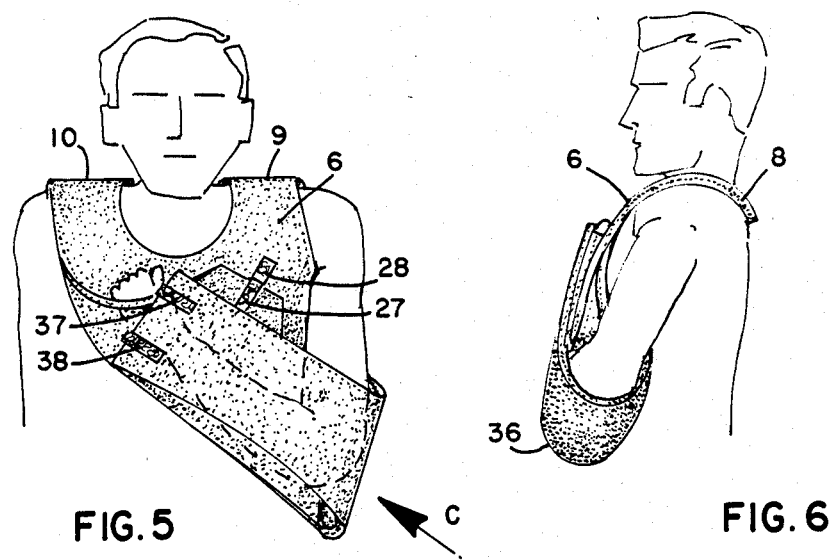
FIG. 5
FIG. 6

SURGICAL SLING

BACKGROUND OF THE INVENTION

This invention relates to surgical slings for an arm, wrist, or hand injury.

More particularly, this invention relates to a one-piece pad sling which includes a head-receiving opening and is equally applicable to support and immobilize either the left or right arm.

In the past, surgical slings were often formed of cloth and included a plurality of straps and buckles or other types of fastening means in order to provide adjustability. Slings which include a head-receiving opening are known in the prior art. Slings which could be reversed to support either the right or left arm are also known in the prior art.

Prior art reversible slings were not easy to put on or remove by the patient without assistance. This problem was particularly acute when it was necessary to adjust the positioning of the arm, wrist, or hand in a preferred upwardly inclined position where the hand of the injured arm or wrist is above the heart while assuring comfortable and secure elbow support.

These prior art difficulties have been substantially overcome by providing a one-piece pad sling of a generally L-shaped configuration. The pad includes a head-receiving opening and has a plurality of attachment means on both sides of the pad. A two-step folding of the pad provides a comfortable entrapment of the injured arm, wrist, or hand in an upwardly inclined orientation against the chest of the wearer while providing elbow support in a comfortable secure manner. The pad is fully reversible in that it can be readily used as a sling to immobilize and secure either arm, wrist, or hand.

SUMMARY OF THE INVENTION

It is an object of this invention to provide a one-piece reversible sling in which either the left or right arm, wrist, or hand of the patient is comfortably immobilized and supported.

It is another object of this invention to provide a one-piece reversible sling which is capable of being put on and taken off by the patient without assistance.

It is a further object of this invention to provide a one-piece, reversible, adjustable sling capable of immobilizing either arm, wrist, or hand by providing, in an adjustable fashion, the securing of the injured arm, wrist, or hand in an upwardly inclined orientation while providing proper elbow support.

It is a still further object of this invention to provide a one-piece, reversible, adjustable sling formed of a cellular or plastic foam pad and including a head-receiving opening which evenly distributes the weight of the injured arm.

Briefly stated and according to an aspect of this invention, a one-piece foam pad of a generally L-shaped configuration is formed which includes a head-receiving opening and a plurality of adjustable attaching means. Once folded, the surgical sling readily supports either injured arm, wrist, or hand in an upwardly inclined position while providing proper elbow support.

BRIEF DESCRIPTION OF THE DRAWINGS

The invention both as to its organization and principles of operation, together with further objects and advantages thereof, may better be understood by referring to the following detailed description of an embodiment of the invention taken in conjunction with the accompanying drawings in which:

FIG. 1 is an elevational view of a first side of a pad prior to folding and the forming of a surgical sling, in accordance with this invention. The second side of the pad is a reversed mirror image thereof.

FIG. 2 is a front view of a patient showing the first fold of the pad of FIG. 1 for a right arm or wrist injury, in accordance with this invention.

FIG. 3 is a front view of the patient of FIG. 2 showing the second and final fold of the pad forming the sling, in accordance with this invention.

FIG. 4 is the front view of a patient showing the first fold of the pad of FIG. 1 for a left arm or wrist injury, in accordance with this invention.

FIG. 5 is a front view of the patient of FIG. 4 showing the second and final fold of the pad forming the sling, in accordance with this invention.

FIG. 6 is a side view of the patient, with the sling of FIG. 5, in accordance with this invention.

DETAILED DESCRIPTION OF THE PREFERRED EMBODIMENT

Throughout the drawings, like characters of reference denote like parts. Referring specifically to FIG. 1, the surgical sling of the present invention is pad 1. The pad 1 is preferably formed of a cellular or plastic foam, such as a medical polyurethane foam, and preferably has a thickness of approximately one-half an inch. The pad 1 includes a generally horizontal arm portion 2 and a generally vertical chest portion 3. The one-piece pad also includes a corner flap portion 4.

The pad 1 is preferably constructed of a foam which has sufficient thickness to cushion the immobilized arm against the chest of the wearer and is of sufficient integrity to be washable, i.e. reusable while still maintaining a sufficient degree of flexibility to allow the ready forming of the sling by the patient using a two-step folding procedure.

FIG. 1 shows a first panel or first side 5 of the pad 1. The opposite side of first side 5 is a second panel or second side 6, seen most readily in the embodiment of FIGS. 4, 5, and 6. The second side 6 of the pad 1 is a reversed mirror image of the first side 5. The location of the attachment means on the second side 6 preferably exactly corresponds to the location of the attachment means on the first side 5.

Disposed through an upper part of the chest portion 3 of the pad 1 is a head-receiving opening 7. The head-receiving opening 7 is of a generally circular or oval shape and is disposed in the upper part of the chest portion 3. The positioning of head-receiving opening 7 provides a back support portion 8 of a predetermined area as well as shoulder portions 9 and 10 of approximately equal areas.

When the head of the patient is positioned through the head-receiving opening 7, and the injured arm is supported by the surgical sling of this invention, the back support portion 8 of the foam pad 1 conforms to the contour of the upper portion of the back of the patient (best seen in FIG. 6). The shoulder support portions 9 and 10 likewise conform to the upper part of the shoulders of the patient. The surgical sling of this invention provides a secure, comfortable support for the injured arm, wrist, or hand without the sling binding against the neck of the patient.

A free edge 11 of chest portion 3 is preferably formed as a straight edge having rounded corners 13 and 14. However, other shapes are within the scope of this invention.

Extending from corner 13 of edge 11 is edge 15. Edge 15 flares outward toward arm portion 2 until a point is reached which is approximately even with the lower part of the head-receiving opening 7. At that point, edge 15 continues as edge 16 by flaring inward, toward corner flap portion 4, until edge 16 mates with arm portion 2. Chest portion 3 also includes an edge 17 which extends from corner 14 of free edge 11 into the corner flap portion 4. Edge 17 is approximately perpendicular to the arm portion 2.

The shape of edges 15, 16, and 17 of chest portion 3 are formed to accommodate the injured arm, wrist, or hand in a preferable upward inclined orientation in a comfortable and secure manner. By having edge 16 flair inward, the upper portion of the injured arm, wrist, or hand may be tightly and comfortably tucked close to the body of the wearer. Whether the left or right arm, wrist, or hand is being immobilized, the respective forearm and hand of the wearer will be supported against the portion of the pad 1 disposed over the chest of the patient in a comfortable, secure fashion.

The corner flap portion 4 has a free edge 18 which is angled with respect to edge 17 of the chest portion 3. The free edge 18 of the corner portion 4 also includes corners 19 and 20, which may be rounded if desired.

The arm portion 2 includes a free edge 21 having corners 22 and 23, which may also be rounded if desired. The arm portion 2 also includes substantially parallel edges 24 and 25.

A plurality of adjustable attachment means are connected to the first side 5, and in the same relative position, to the second side 6. The adjustable attaching means are connected to the sides 5 and 6 of the pad 1 in a variety of manners well known in the art. Preferably, the adjustable attachment means are connected to the pad 1 by adhesive bonding.

The attachment means preferably take the form of mating tapes or strips of a looped pile fabric and a resilient hook fabric. Such fabrics are well known in the art and are sold under the trade name of Velcro. The actual shape or size of the attaching means may vary widely. However, it is preferable to have the attachment means in the form of one or more strips in order to provide the desired fold orientation and adjustability feature of this invention. Further, it is preferred to have the hook portion of the attachment means or fasteners, i.e. the active fastener, be that portion of the attachment means which will not usually come into contact with clothing in order to prevent unnecessary snagging or the like.

A first attachment means for securing the first fold for the right arm sling of this invention is made up of first loop fastener 26 and first hook fastener 27, both attached to the first side 5 of the pad 1. First loop fastener 26 is positioned at an angle in a lower part of the chest portion 3 of pad 1 and is approximately axially aligned with mating first hook fastener 27. First hook fastener 27 is preferably aligned with first loop fastener 26 and is located on the first side 5 of pad 1 at the corner flap portion 4.

As best seen in FIG. 2, the folding of the corner flap portion 4 by the patient in the direction of arrow A causes the aligned mating of first hook fastener 27 with first loop fastener 26 around the injured right arm. Preferably, the corner flap portion 4 is folded, in the direction of Arrow A, to comfortably and securely maintain the arm in an upward inclined position so that the hand is above the heart.

When it is desired to immobilize the left arm, wrist, or hand, as shown in FIGS. 4 and 5, the pad 1 is placed over the head through the head-receiving opening 7 with the first side 5 of pad 1 next to the body of the patient. That is, the pad 1 is put over the head of the patient so that the arm portion 2 extends in front of the patient and is on the same side as the injured arm, wrist, or hand.

A second attachment means is made up of a second loop fastener 28 and second hook fastener 29, both attached to the second side 6 of pad 1. Second attachment means work in the same manner for the left arm, as first attachment means works for the right arm. Second loop fastener 28 is positioned at an angle in the lower part of the chest portion 3 of pad 1 and is approximately axially aligned with mating second hook fastener 29. Second hook fastener 29 is attached to the second side 6 of pad 1 at the corner flap portion 4. As best seen in FIG. 4, the corner flap portion 4 is folded by the patient in the direction of arrow B, thereby mating second loop fastener 28 with second hook fastener 29 to form a first fold attachment.

For the sake of manufacturing convenience and durability, first hook fastener 27 and second hook fastener 29 may be formed from the same strip folded around free edge 18 of corner flap portion 4.

The first attachment means made up of first loop fastener 26 and first hook fastener 27 on first side 5 and the second attachment means made up of second loop fastener 28 and second hook fastener 29 on the second side 6 are preferably formed as elongated strips. The specific point of attachment may vary, depending upon the size of the individual or the desired angle of incline of the immobilized forearm. Preferably, the forearm is immobilized at an angle of approximately 45° with respect to the upper arm to result in the desired placement of the hand above the heart.

A third attachment means securing the second fold for the right arm sling and a fourth attachment means securing the second fold for the left arm sling are preferably formed of approximately parallel strips of mating hook/loop material.

The mating of the relevant strips forming the third and fourth attachment means are also adjustable by the patient depending on the positioning of the mating hook and loop strips. More specifically and referring to FIGS. 2 and 3, a third attachment means includes loop strips or fasteners 34 and 35 attached, in parallel, to the corner flap portion 4 of side 6 of pad 1. The loop fasteners 34 and 35 are located approximately perpendicular to the second hook fastener 29. Located on the first side 5 of pad 1 are mating hook strips or fasteners 37 and 38. The mating hook fasteners 37 and 38 are located approximately parallel and extend to the edge 21 of arm portion 2 of pad 1. As best seen in FIGS. 2 and 3, after the first fold has been completed, hook fasteners 37 and 38 mate with loop fasteners 34 and 35, respectively, when folded, by the patient, in the direction of arrow D, as shown in FIG. 3. The mating of components of the third attachment means is performed subsequent to that of the components of the first attachment means to form a comfortable and secure elbow support section for the right arm analogous to that for the left arm as shown by section 36 seen in FIG. 6.

In like manner, when dealing with the left arm as shown in FIGS. 4 and 5, a fourth attachment means secures the second fold. Fourth attachment means includes loop strips for fasteners 30 and 31 attached in parallel to corner flap portion 4 of side 5 of pad 1. The loop fasteners 30 and 31 are located approximately perpendicular to the first hook fastener 27. Located on the second side 6 of pad 1 are mating hook fasteners 32 and 33. The mating hook fasteners 32 and 33 are located approximately parallel and extend to the edge 21 of arm portion 2 of pad 1. For the sake of manufacturing convenience and durability, strips 32 and 38 and strips 33 and 37 may be formed as a single strip folded around free edge 21 of arm position 2. As best seen in FIGS. 4, 5, and 6, after the first fold has been completed, hook fasteners 32 and 33 mate with loop fasteners 30 and 31, respectively, when folded, by the patient, in the direction of arrow C, as shown in FIG. 5. The mating of the components of the fourth attachment means is performed subsequent to that of the components of the second attachment means to form a comfortable and secure elbow support section 36, seen in FIG. 6, for the left arm.

While an embodiment and application of the invention has been shown and described, it will be apparent to those skilled in the art that many more modifications are possible without departing from the inventive concepts herein described. The invention, therefore, is not to be restricted except as is necessary by the prior and by the spirit of the appended claims.

What is new and desired to be secured by Letters Patent of the United States is:

1. A reversible surgical sling for either injured arm, wrist, or hand of a patient formed by folding a one-piece, flexible member, having a first and second side and having a predetermined thickness, wherein said one-piece flexible member, in layout, comprises:

a vertical portion having a free end;

a horizontal portion having a free end;

a corner portion connecting said vertical portion to said horizontal portion at an approximate right angle;

a head-receiving opening formed in said vertical portion for mounting said flexible member over the head of the patient from either the first or second side of said flexible member to orient said vertical portion of said flexible member in front of the chest of the patient and to orient said horizontal portion to extend under the arm and on the same side of the patient as the injured arm, wrist, or hand;

first fastener means connected to said first side of said corner portion of said flexible member;

second fastener means connected to said first side of said vertical portion of said flexible member for coupling with said first fastener means to form a first fold of said flexible member abut the right arm for immobilizing the injured arm, wrist, or hand in an upwardly inclined position wherein the right hand is approximately above the heart of the patient;

third fastener means connected to said first side of said horizontal portion of said flexible member;

fourth fastener means connected to said second side of said corner portion of said flexible member for coupling with said third fastener means to form a second fold of said flexible member about the right elbow for providing right elbow support;

fifth fastener means connected to said second side of said corner portion of said flexible member;

sixth fastener means connected to said second side of said vertical portion of said flexible member for coupling with said fifth fastener means to form a first fold of said flexible member about the left arm for immobilizing the injured arm, wrist, or hand in an upwardly inclined position wherein the left hand is approximately above the heart of the patient;

seventh fastener means connected to said second side of said horizontal portion of said flexible member; and eighth fastener means connected to said first side of said corner portion of said flexible member for coupling with said seventh fastener means to form a second fold of said flexible member about the left elbow for providing left elbow support.

2. The reversible sling as in claim 1 wherein said flexible member is a cellular plastic foam.

3. The reversible sling as in claim 2 wherein said foam is a polyurethane foam.

4. The reversible sling as in claim 3 wherein the predetermined thickness of said foam is approximately one-half inch.

5. The reversible sling as in claim 1 wherein said vertical portion of said flexible member includes a back support portion disposed above said head-receiving opening and said vertical portion also includes first and second shoulder support portions disposed on either side of said head-receiving opening, said back support portion conforming to the contour of the upper portion of the back of the patient.

6. The reversible sling as in claim 1 wherein all of said fastener means are connected to said flexible member by adhesive bonding.

7. The reversible sling as in claim 1 wherein all of said fastener means are adjustable.

8. The reversible sling as in claim 7 wherein all of said fastener means are stiprs of hook and loop tape.

9. The reversible sling as in claim 8 wherein said first and fifth fastener means are integrally formed about the free edge of said corner portion of said flexible member.

10. The reversible sling as in claim 9 wherein said third and seventh fastener means are integrally formed about said free end of said horizontal portion of said flexible member.

* * * * *